(12) United States Patent
Janku et al.

(10) Patent No.: US 11,654,038 B2
(45) Date of Patent: May 23, 2023

(54) STENT DELIVERY CATHETER SYSTEM WITH A HELICOID HYPOTUBE

(71) Applicant: CORDIS US CORP., Miami Lakes, FL (US)

(72) Inventors: Joy Janku, Miami Lakes, FL (US); Cesar Rincon, Miami Lakes, FL (US)

(73) Assignee: CORDIS US CORP., Miami Lakes, FL (US)

( * ) Notice: Subject to any disclaimer, the term of this patent is extended or adjusted under 35 U.S.C. 154(b) by 352 days.

(21) Appl. No.: 16/863,712

(22) Filed: Apr. 30, 2020

(65) Prior Publication Data

US 2020/0360164 A1 Nov. 19, 2020

Related U.S. Application Data

(60) Provisional application No. 62/846,844, filed on May 13, 2019.

(51) Int. Cl.
| | |
|---|---|
| *A61F 2/966* | (2013.01) |
| *A61F 2/95* | (2013.01) |
| *A61F 2/962* | (2013.01) |
| *A61M 25/00* | (2006.01) |

(52) U.S. Cl.
CPC ............ *A61F 2/9517* (2020.05); *A61F 2/962* (2013.01); *A61F 2210/0014* (2013.01); *A61M 25/0074* (2013.01); *A61M 2025/0042* (2013.01)

(58) Field of Classification Search
CPC . A61F 2/9517; A61F 2/962; A61F 2/95–2/97; A61F 2/2418; A61F 2/2427; A61F 2/243; A61F 2/2433; A61F 2/2436; A61F 2/2439; A61F 2/2466; A61M 25/0074; A61M 2025/0042
USPC ................................................ 623/1.11–1.54
See application file for complete search history.

(56) References Cited

U.S. PATENT DOCUMENTS

| | | | |
|---|---|---|---|
| 2007/0010867 A1* | 1/2007 | Carter | A61F 2/966 606/108 |
| 2007/0244540 A1* | 10/2007 | Pryor | A61F 2/966 623/1.11 |

* cited by examiner

*Primary Examiner* — Kathleen S Holwerda
(74) *Attorney, Agent, or Firm* — ArentFox Schiff LLP (57) ABSTRACT

Various embodiments for a stent delivery device or catheter system that includes a stent disposed between an inner shaft and an outer sheath. A housing is coupled to the inner shaft and outer sheath with a rotary reel disposed in the housing and configured for rotation with respect to the housing. A hypotube is disposed in the housing and fixed thereto with the inner shaft extending into the opening of the hypotube and the outer sheath enshrouding a portion of the hypotube. Rotation of the rotary reel in a first direction pulls the outer sheath over the hypotube along the generally circular path to retract the outer sheath from the stent. In some embodiments, a rapid deployment mechanism allows for retracdtion of the outer sheat at an increased rate.

9 Claims, 8 Drawing Sheets

STENT DELIVERY CATHETER SYSTEM WITH A HELICOID HYPOTUBE

BACKGROUND

It is well known to employ various intravascular endoprostheses delivered percutaneously for the treatment of diseases of various body vessels. These types of endoprosthesis are commonly referred to as "stents". A stent (which includes covered stents or stent-graft) is a generally longitudinal tubular device of biocompatible material, such as stainless steel, cobalt-chromium, nitinol or biodegradable materials, having holes or slots cut therein to define a flexible framework so they can be radially expanded, by a balloon catheter or the like, or alternately self-expanded due to its shape memory characteristic of the material within a biological vessel. The stents are usually configured as a series of hoops with each defined by cylinder-like framework. The framework is usually a series of alternating sequence of struts with a vertex between each pair of struts and configured so that the vertex of one hoop facing a vertex of the adjacent hoops may be connected together. The struts are configured to move and thereby allow the stent to be compressed or "crimped" into a smaller outer diameter so that they can be mounted inside a delivery system.

The delivery systems is used to convey the stent to a desired location for treatment, and then deploy them in position. Many such stents are resiliently compressed to a smaller initial size for containment, protection, storage and eventual delivery from inside a catheter system. Upon deployment, the stents may resiliently self-expand to a larger deployed size.

A successful example of a delivery catheter system, in this case for a self-expanding stent, is described in U.S. Pat. No. 6,019,778 entitled "Delivery Apparatus For A Self-Expanding Stent," to Wilson et al. issued Feb. 1, 2000. The disclosure of this patent is incorporated by reference in the present application, and generally discloses a flexible catheter system shown in a representative diagrammatic form in FIG. 10 of Wilson, including coaxially arranged inner and outer catheter members, each having a hub affixed to its proximal end. The outer sheath is described in the '778 patent as an elongated tubular member having distal and proximal ends, which is made from an outer polymeric layer, an inner polymeric layer, and a braided reinforcing layer between them. The inner shaft is described in the '778 patent as being located coaxially within the outer sheath and has a flexible tapering distal end, which generally extends distally beyond the distal end of the outer sheath. The inner shaft member also is shown as including a stop which is positioned proximal from the distal end of the outer sheath. A self-expanding stent is located within the outer sheath, and is located between the stop on the inner shaft member and the outer sheath distal end. To deploy the stent the outer sheath is withdrawn by a physician in a proximal direction, while the inner shaft member is held in position.

Additional examples of different types of known self-expanding stent delivery systems are shown in U.S. Pat. No. 4,580,568 issued to Gianturco on Apr. 8, 1986; as well as U.S. Pat. No. 4,732,152 issued to Wallsten et al., on Mar. 22, 1988.

In operation, these known stent delivery systems are generally advanced within a body of a patient along a desired vascular path or other body passageway, until the stent within the catheter system is located at a desired site for treatment. While watching the relative positions of the stent and the catheter system components with respect to a stenosis on a video x-ray fluoroscopy screen, the physician holds the proximal hub attached to the inner shaft member in a fixed position with one hand, while simultaneously gently withdrawing the proximal hub attached to the outer tubular sheath with the other hand.

For several reasons, this deployment operation may require some measure of delicate skill. For example, among these reasons is the dynamic blood flow at the desired site for treatment, which may be further disrupted by the presence of a lesion or stenosis to be treated. Another factor is the gradual resilient expansion of a stent as the outer sheath is retracted. This gradual expansion presents an opportunity for a possible reverse "watermelon-seed" phenomenon to occur. This reverse watermelon-seed effect may cause the resilient stent to tend to push the outer sheath back in a proximal direction with a force that tends to change as the sheath is progressively retracted.

As a result, the physician may need to accurately hold the two proximal hubs in a specific relative position, holding them against this expansion force, while attempting to very accurately position the stent up until contact with the anatomy. One of the possibilities that may affect the positioning of the deployed stent is that the inner shaft should preferably be held stationary in the desired position. If the physician's hand that holds the inner shaft hub does inadvertently move during deployment, it is possible that the stent may be deployed in a non-optimum position.

Another possible factor is that the inner and outer catheter shaft members, like any other elongated object, do not have infinite column strength, which may present an opportunity for the position and movement of each proximal hub to differ from the position and movement of the respective distal ends of the inner and outer shaft members. Yet another factor is that the position of the stent may be adjusted up until the point at which a portion of the expanding portion of the stent touches the sidewalls of the body passage, so that the position of the stent should preferably be carefully adjusted until immediately before a portion of the stent touches the anatomy.

Some known catheter systems require two-handed operation, such as those with a pair of independent hubs, one hub on the inner and outer shaft member, respectively. Other known catheter systems include a pistol and trigger grip, with a single mode of deployment, involving a single trigger pull to deploy the associated stent.

SUMMARY OF THE DISCLOSURE

Applicant has devised a stent delivery system that includes a catheter tip, inner shaft, outer sheath and a stent. The catheter tip is coupled to the inner shaft and an outer sheath with a stent disposed between the inner shaft and the outer sheath. The inner shaft and the outer sheath extends from a distal end to a proximal end. The system includes a housing coupled to the inner shaft and outer sheath as well as a rotary reel disposed in the housing and configured for rotation with respect to the housing. The rotary reel has a connector fixed to the outer sheath. The system includes a hypotube disposed in the housing and fixed thereto with the inner shaft extending into the opening of the hypotube and the outer sheath enshrouding a portion of the hypotube. The hypotube extends from a first end of the housing to a second end of the housing in a generally circular path defined by the rotary reel such that rotation of the rotary reel in a first direction pulls the outer sheath over the hypotube along the generally circular path to retract the outer sheath from the stent.

Applicant has also devised a catheter system that includes a catheter tip, inner shaft, and an outer sheath. The catheter tip is coupled to the inner shaft and an outer sheath with the outer sheath surrounding a portion of the outer surface of the inner shaft. The inner shaft and the outer sheath extend from a distal end to a proximal end. The system includes a housing coupled to the inner shaft and outer sheath as well as a rotary reel disposed in the housing and configured for rotation with respect to the housing. The rotary reel has a connector fixed to the outer sheath. The system includes a hypotube disposed in the housing and fixed thereto with the inner shaft extending into the opening of the hypotube and the outer sheath enshrouding a portion of the hypotube. The hypotube extends from a first end of the housing to a second end of the housing in a generally circular path defined by the rotary reel such that rotation of the rotary reel in a first direction pulls the outer sheath over the hypotube along the generally circular path with respect to the inner shaft.

For each of the embodiments described above, the following features can be utilized in various permutations with each of the embodiments. For example, a thumbwheel can be mounted to the housing and connected to the rotary reel; alternatively, a ratchet can be disposed between the thumbwheel and the housing so that the thumbwheel is rotatable only in the first direction; furthermore, a flexible member can connect the thumbwheel to the reel to allow rotation of the reel at a selected speed ratio (depending on the diameter of the thumbwheel with respect to the rotary reel) and such flexible member can be selected from a group that may include a belt, rope, wire or combinations thereof.

Some embodiments may be configured for rapid deployment of the stent by allowing for retraction of the outer sheath at an increased rate. For example, the flexible member connecting the thumbwheel is secured to a spiral track of the rotary reel so that a rate of retraction of the outer sheath increases when withdrawn in a proximal direction. As another illustration, a tubular actuator is secured at its distal end secured to the rotary reel and is coaxially disposed over a proximal portion of the inner shaft, so that proximal motion of of the tubular actuator causes rotation of the rotary reel in the first direction to retract the outer sheath with respect to the inner shaft.

This disclosure also includes a method for stent delivery. A catheter tip coupled to an inner shaft and an outer sheath with a stent disposed between the inner shaft and the outer sheath may be provided. The inner shaft and the outer sheath extend from a distal end to a proximal end, with a housing coupled to the inner shaft and outer sheath. A rotary reel is disposed in the housing and configured for rotation with respect to the housing, the rotary reel having a connector fixed to the outer sheath and a hypotube disposed in the housing and fixed thereto with the inner shaft extending into the opening of the hypotube and the outer sheath enshrouding a portion of the hypotube, the hypotube extending from a first end of the housing to a second end of the housing in a generally circular path defined by the rotary reel. The stent is positioned at a desired location within a patient and the rotary reel is rotated in a first direction to pull the outer sheath over the hypotube along the generally circular path to retract the outer sheath from the stent. The method may also include retracting the outer sheath at an increased rate to rapidly deploy the stent.

These and other embodiments, features and advantages will become apparent to those skilled in the art when taken with reference to the following more detailed description of the exemplary embodiments of the invention in conjunction with the accompanying drawings that are first briefly described. As well, it is intended that these embodiments, features and advantages may be claimed in this or additional applications for patents.

BRIEF DESCRIPTION OF DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The term "stent" is intended to encompass an uncovered framework as well as one that is covered by a suitable material (e.g., stent-graft). The term "proximal" is used to denote the location closer to the operator and "distal" is used to denote a location further away from the operator or the health care provider.

Figure 1A:
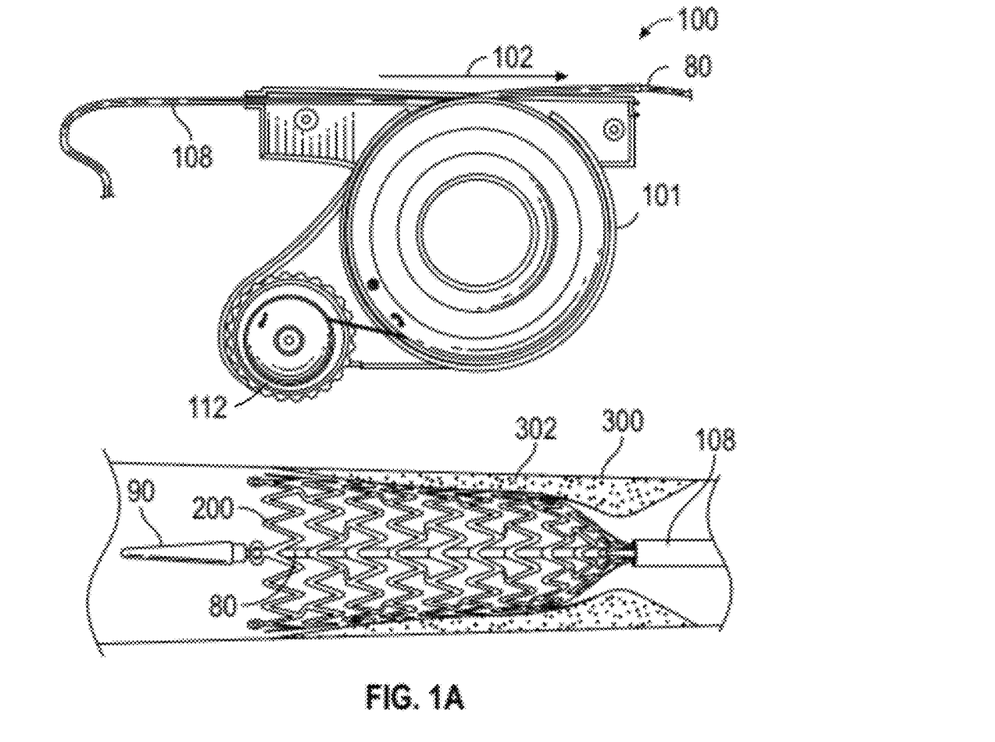
FIG. 1A illustrates a system view of a handle according to an embodiment as well as a representation of the operation of the system.

Referring now to the figures wherein like numerals indicate the same element throughout the views, there is shown in FIG. 1A of a handle a stent delivery system 100. The system 10 includes a catheter tip 90 coupled to an inner shaft 80 and an outer sheath 108 with a stent 200 disposed between the inner shaft 80 and the outer sheath 108. Note that the inner shaft 80 and the outer sheath 108 extend from a distal end to a proximal end in FIG. 1A. Referring to the proximal end of the system 100, there is provided a housing 101. The housing 101 is intended to allow for the inner shaft 80 and outer sheath 108 to be mounted or coupled to the housing 101. A rotary reel or rotatable rotary reel 104 is mounted in the housing 101 shown here in FIG. 1C.

Figure 1B:
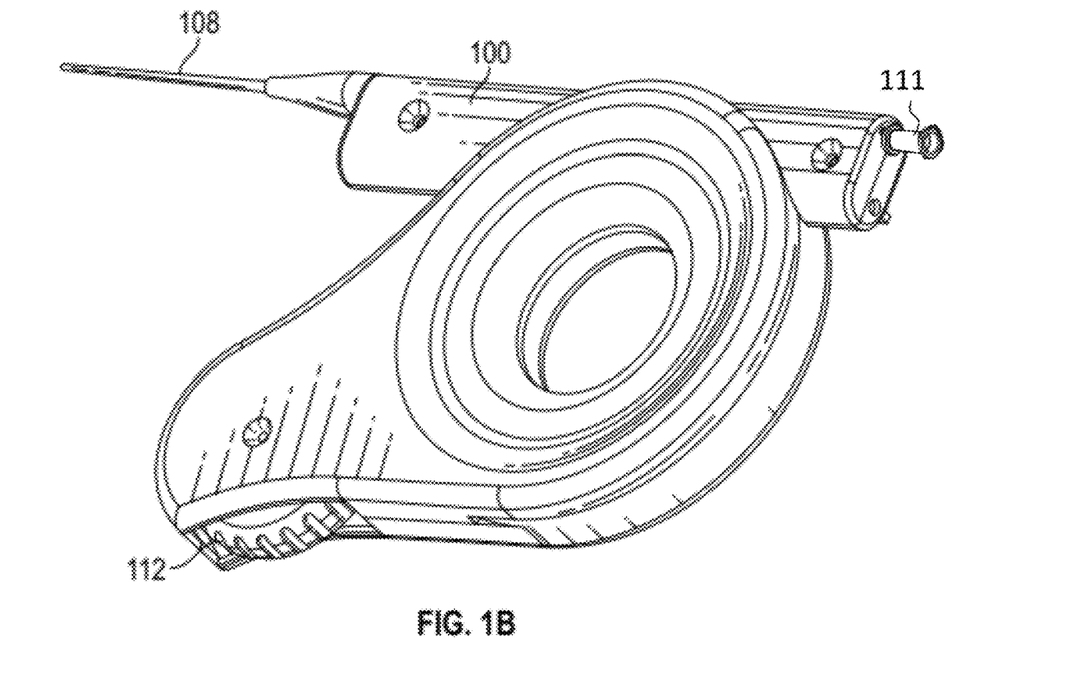
FIG. 1B illustrates a perspective view of the handle.
Figure 1C:
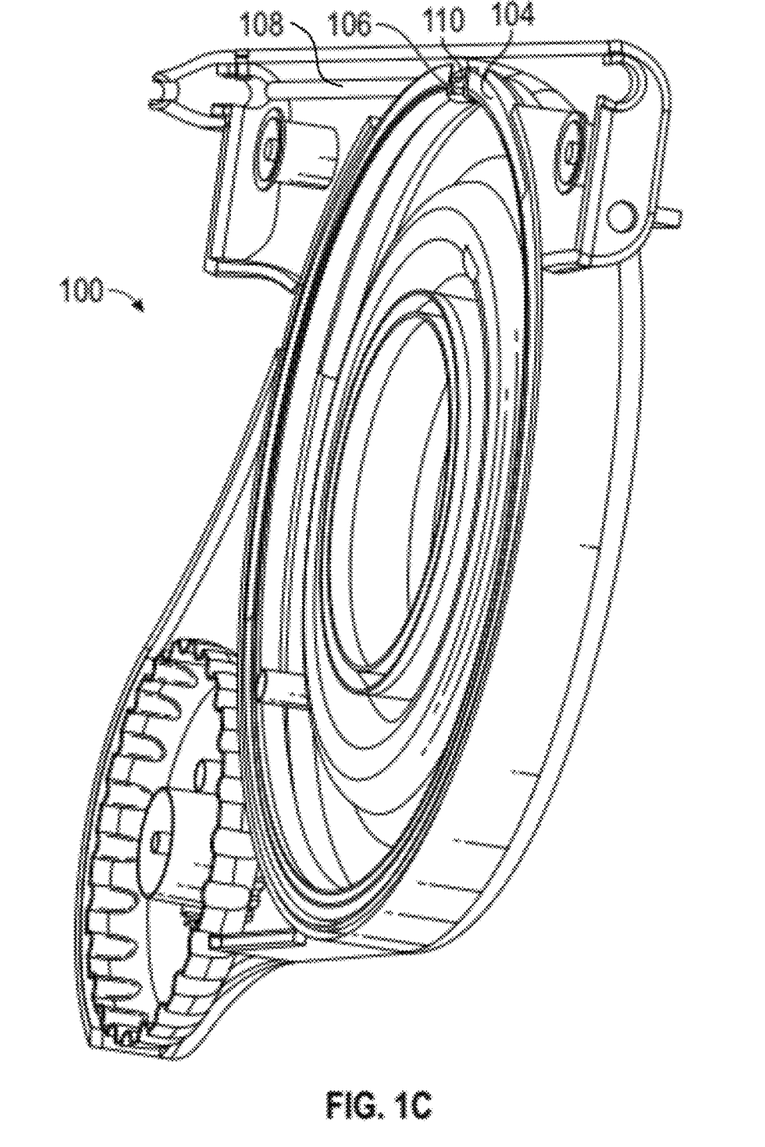
FIG. 1C illustrates a sectioned perspective view to show the inside of the handle.
Figure 1D:
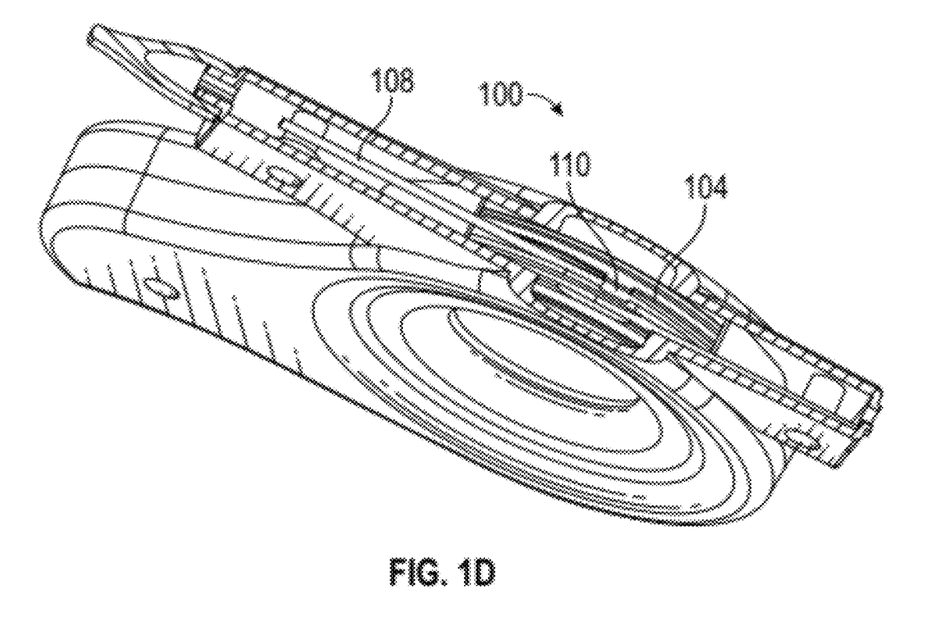
FIG. 1D illustrates a top down perspective view with the top of the handle sectioned to show the outer sheath and hypotube mounted on the rotary reel.

In FIGS. 1C and 1D, rotary reel 104 is configured such that rotary reel 104 rotates relative to the housing 101. Rotary rotary reel 104 is provided with a connector boss 106 fixed to the outer sheath 108 such that when rotary reel 104 rotates, outer sheath 108 is pulled over a hypotube 110 that is disposed in a wound configuration around the reel. The inner diameter of outer sheath 108 is sized to fit over hypotube 110. As shown in FIG. 1B, a thumbwheel 112 is provided to allow for retraction of the outer sheath 108 as described below by rotating rotary reel 104.

Figure 2A:
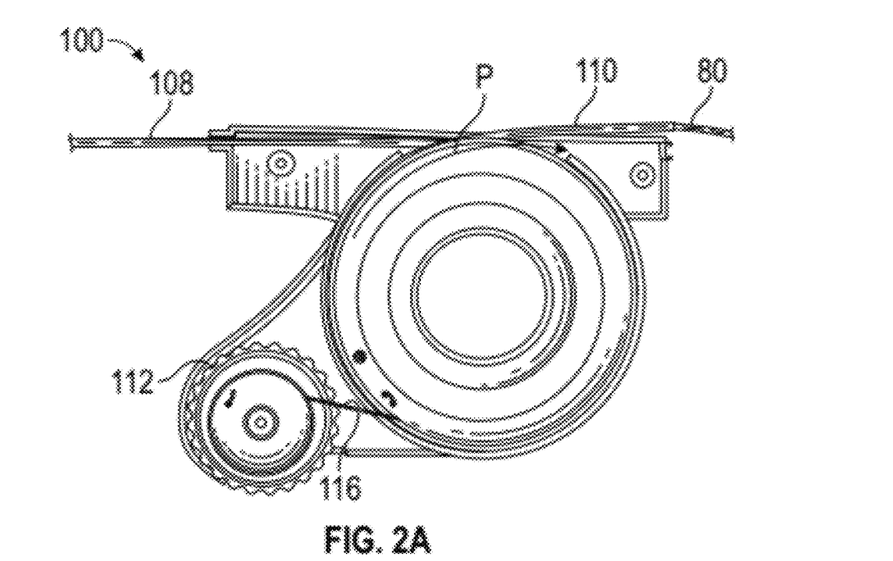
FIG. 2A is a photograph of a prototype of handle of FIG. 1A with one-half of the housing removed to show the thumbwheel, hub, outer sheath and hypotube.
Figure 2B:
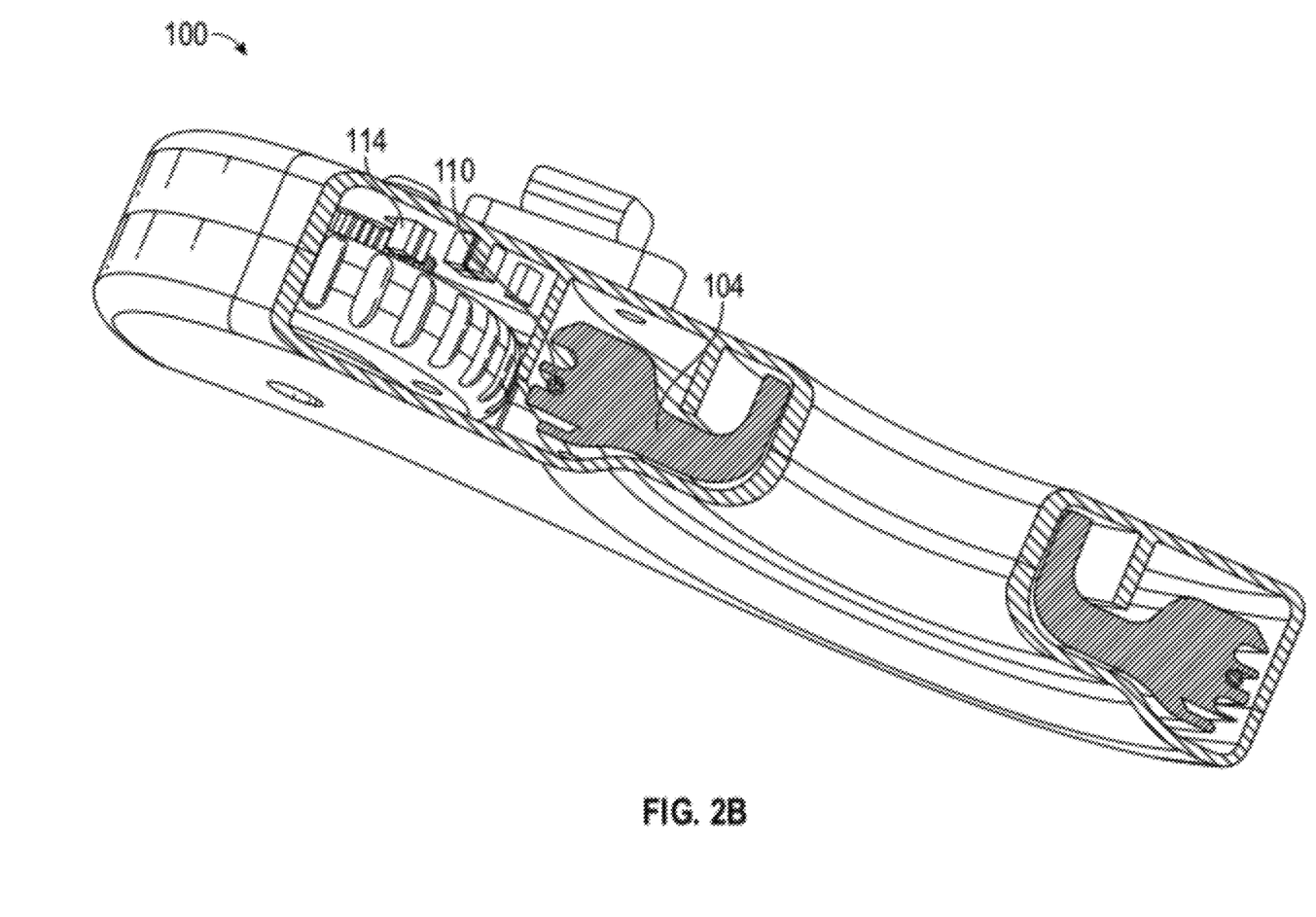
FIG. 2B is a sectioned perspective view to show the thumbwheel as well as the one-way ratchet mechanism for the thumbwheel.

As shown in FIG. 2A, the hypotube 110 is disposed in the housing 101 and fixed thereto the housing 101 so that the hypotube 110 does not move when the rotary reel 104 is rotated. Note that the inner shaft 80 extends into the opening of the hypotube from the distal end of the hypotube 110 and out of the hypotube 110 at the proximal end. On the other hand, note that the outer sheath 108 is pulled over (e.g., like a sock over the hypotube) to enshroud a portion of the hypotube 110. The hypotube 110 extends from a first end of the housing to a second end of the housing, being wound in a generally circular path P defined by the rotary reel 104 such that rotation of the rotary reel 104 in a first direction (e.g., clockwise in the example) with respect to the stationary hypotube 110 pulls the outer sheath 108 over the stationary hypotube 110 along the generally circular path P to retract the outer sheath 108 from the stent 200. For example, hypotube 110 may define one or more turns around rotary reel 104. By disposing inner shaft 80 within hypotube 110 while outer sheath 108 travels coaxially over hypotube 110, motion of outer sheath 108 is decoupled from inner shaft 80, helping to minimize or prevent movement of stent 200 from its desired placement. Any suitable technique can be used to ensure that the hypotube is stationary with respect to the housing such as for example, adhesives or interference tabs between the hypotube 110 and the housing 100. Alternatively, or in addition, a luer lock 111 (as shown in FIG. 1B) or equivalent structure may be secured to housing 101, to mate with and stabilize hypotube 110 while also providing a flushing function if desired. The hypotube 110 can be formed of a suitable material such as medical grade metal (stainless steel) or polymers. The hypotube 110 is preferably formed in a helicoid configuration but it should be noted that any generally circular path can be utilized. As shown in FIGS. 1D and 2B for example, rotary reel 104 may also have a track formed along its outer radius to define the circular path in which hypotube 110 is disposed.

To facilitate retraction of the outer sheath 108 over the hypotube 110, a thumbwheel 112 can be mounted to the housing 101 and connected to the rotary reel 104 at a suitable speed ratio. Additionally, a ratchet 114 (FIG. 2B) can be provided between the thumbwheel and the housing so that the thumbwheel is rotatable only in the first direction. Rotation of the rotary reel 104 can be accomplished by a gear train from the thumbwheel 112 to the rotary reel 104. In the preferred embodiment, a flexible member 116 (e.g., belt, rope, wire, string and the like) can be used to transfer the rotation of the thumbwheel 112 to the reel 104.

Figure 3:
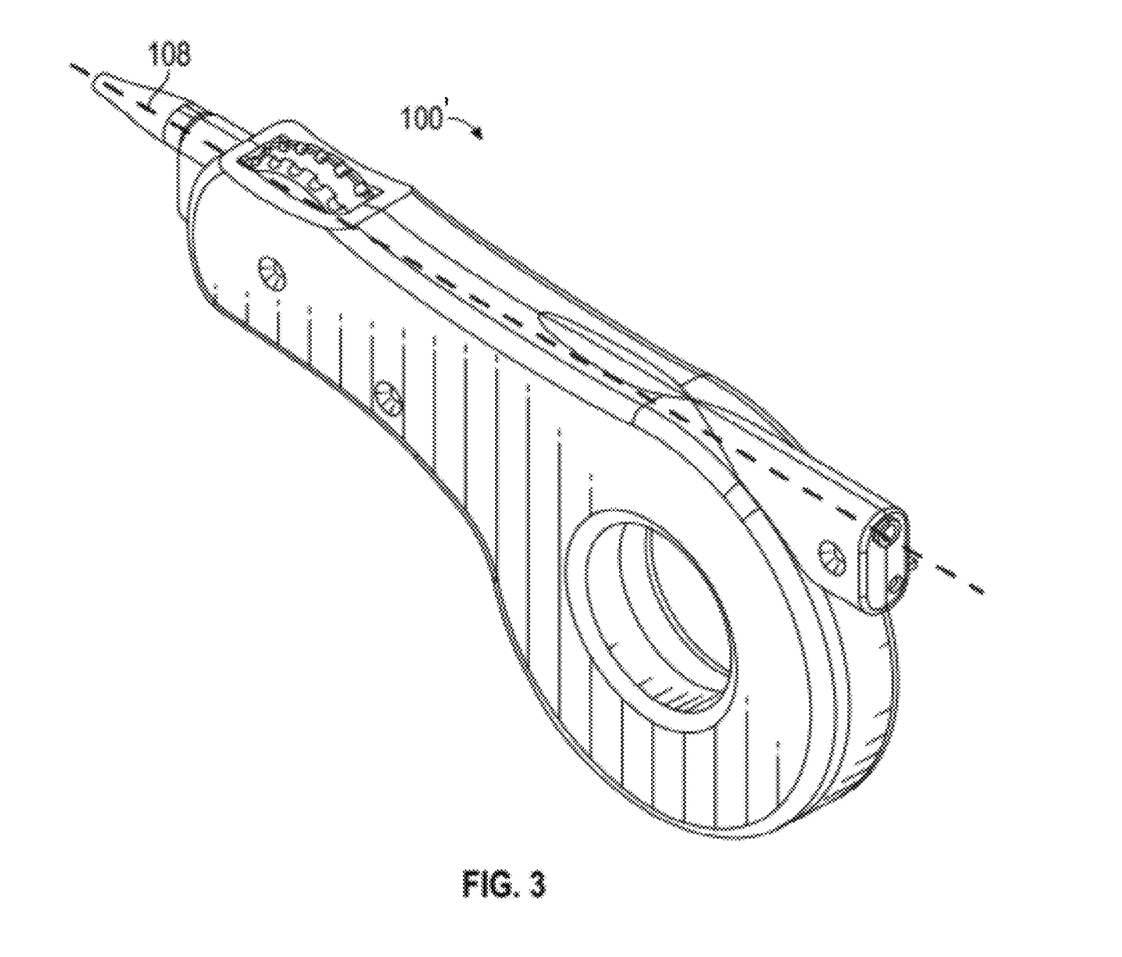
FIG. 3 illustrates another embodiment of FIG. 1A with a longer housing as well as a thumbwheel mounted close to the outer sheath.
Figure 4:
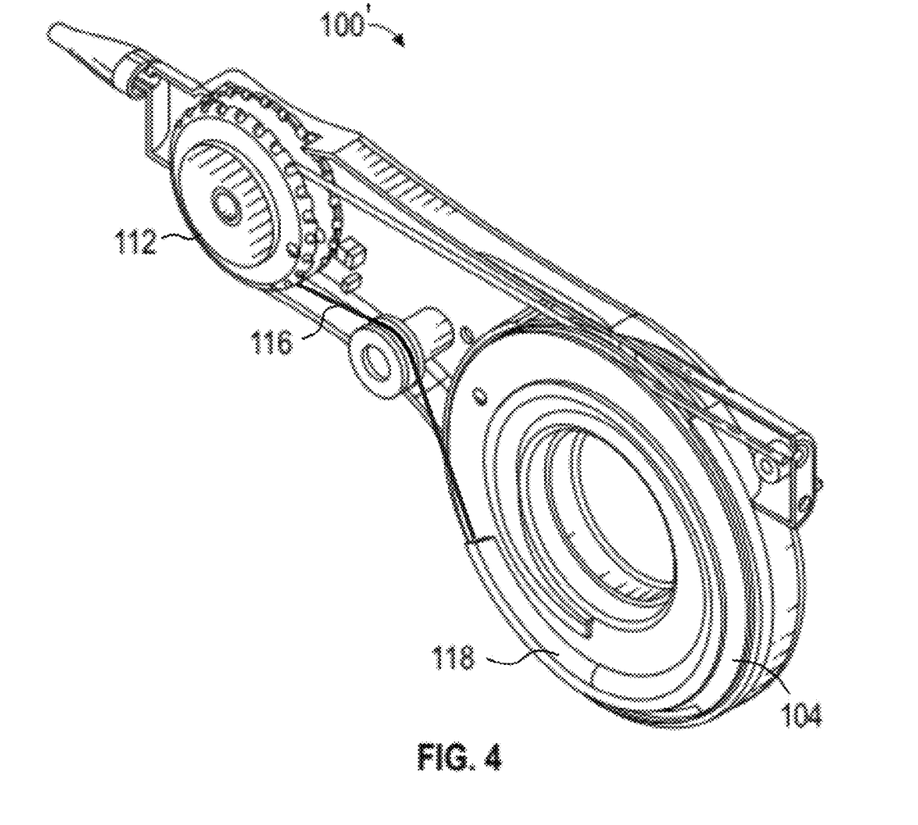
FIG. 4 is a sectioned view of FIG. 3 showing a thumbwheel and rotary reel configured for rapid deployment.
Figure 5:
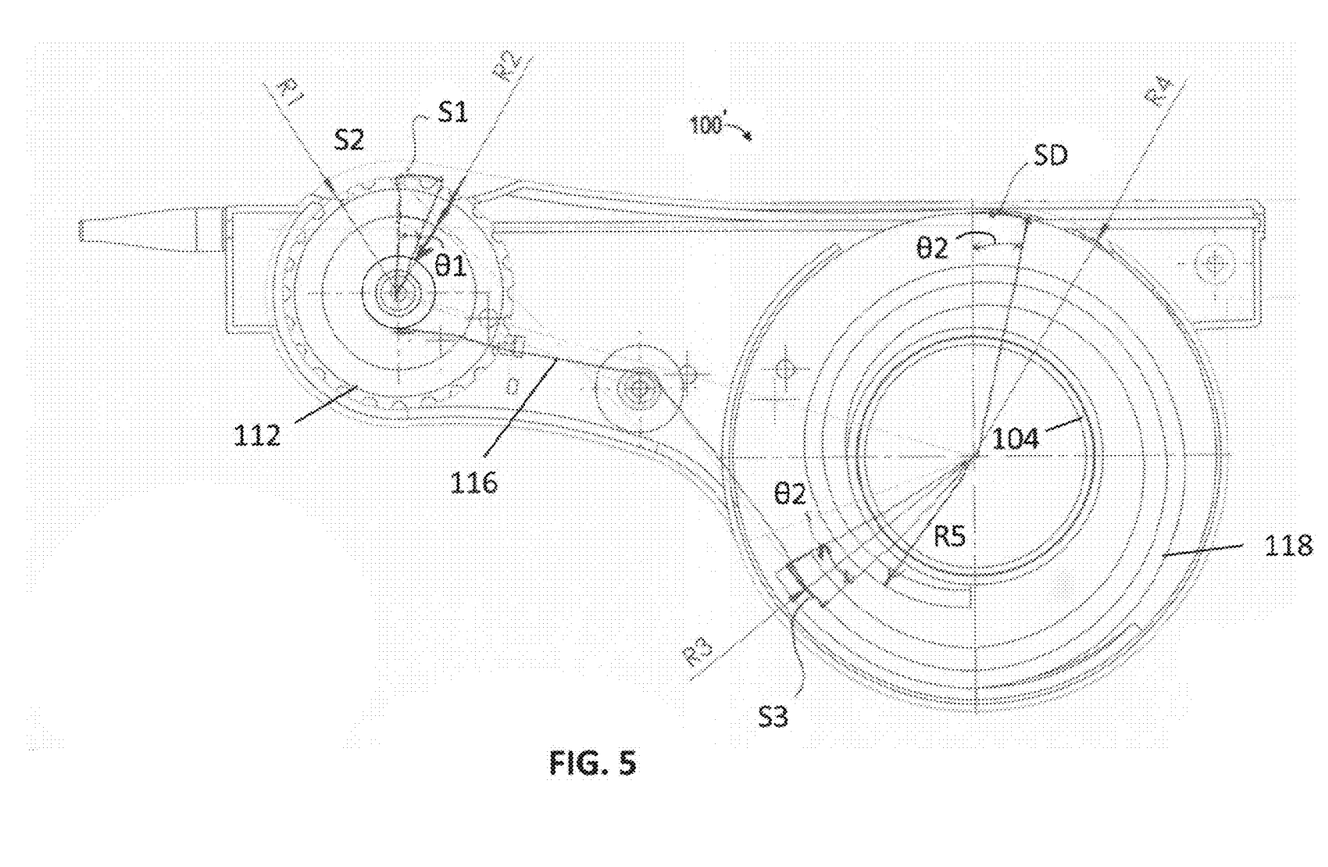
FIG. 5 schematically depicts how characteristics of the embodiment of FIG. 3 relate to the deployment rates.

Other form factors can be utilized using the inventive principles shown and described herein. For example, the rotary reel 104 can be mounted more to the proximal end of the handle 100 to provide better balance (for the operator) in a first alternative handle design 100', shown here in FIGS. 3 and 4. In yet another alternative embodiment, the handle can have an intermediate overall length, as shown here for handle 100" in FIG. 5. In the embodiments of FIGS. 3-5, it is noted that the thumbwheel is disposed adjacent the outer sheath 108 rather than offset from the outer sheath as in FIG. 1A.

In operation, the distal end of the medical device delivery system 10 (as well as 100' or 100") is preferably directed into a patient via a body passageway 300 of the patient. The medical device delivery system 10 may preferably follow along a guidewire (not shown) or travel through a previously placed guiding catheter (not shown), until the distal tip 90 is at a desired location in the body vessel 300 for treatment. As shown in FIG. 1A, the distal tip 90 has preferably crossed the site of a lesion or stenosis 302. When the device is properly in an initial position (FIG. 1A), the physician releases or breaks off the lock of the thumbwheel (not shown for brevity). The lock may be releasable only once, or may be capable of repeatedly being engaged and released. Such a locking mechanism preferably resists inadvertent or accidental movement or retraction of the stent delivery system components during packaging, sterilization, shipping, storage, handling and preparation.

After the lock is released, the thumbwheel 112 can be rotated (FIG. 2A) such that the outer sheath 108 is retracted slowly towards the operator due to the rotary reel 104 rotating and pulling the outer sheath 108 over the stationary hypotube in a similar manner as that of a sock over a tube. Lubricants in the form of coatings or saline solution can be used to reduce frictional contact between the outer sheath 108 and the hypotube 110. The use of the thumbwheel as well as the rotary reel and hypotube allows precise and sensitive adjustment when the physician is attempting to pull the outer sheath 108 back slightly. This small movement exposes a small portion of the medical device, in this case a stent 200, as shown in FIG. 1A. In this configuration, the handle 100 will hold the outer sheath 108 in position relative to the inner wire 80, resisting further inadvertent expansion of the stent 200. The physician then has the time and flexibility of procedure to selectively optimize and make any final adjustments to the position of the medical device and delivery system within the desired site, as illustrated in FIG. 1A. This precise adjustment of the position of the stent 200, before any portion of the stent 200 touches the body passage or vessel 300 in a manner that might inhibit further positional adjustment, is preferable.

When the physician is satisfied with the positioning, as it appears on a fluoroscopic x-ray video screen, the physician may continue to rotate the thumbwheel 112 to further withdraw the outer sheath 108.

Upon initial contact of the stent 200 with the vessel wall 302, or when the stent is 200 expanded sufficiently to independently hold its position, or at any desired point, some embodiments of this disclosure allow for substantially greater retraction speed for rapid deployment of the stent.

This second mode of withdrawing the outer sheath 108 allows relatively large-scale and rapid movement, at whatever speed the physician wishes, to quickly deploy the medical device.

For example, in the embodiment shown in FIGS. 3 and 4, thumbwheel 112 may be connected by flexible member 116 to the rotary rotary reel 104 along spiral track 118. Correspondingly, during initial retraction of outer sheath 108 stages, rotation of thumbwheel 112 is transmitted by flexible member 116 to a portion of track 118 having a relatively greater diameter, allowing for improved control over the retraction speed. Subsequently, as outer sheath 108 is retracted, the force transmitted by flexible member 116 engages an increasingly smaller diameter of 118, speeding up the rate of retraction. One illustration of suitable equations for determining the relative diameters of thumbwheel 112 and spiral track 118 is depicted in FIG. 5, but it will be appreciated that other ratios may be employed depending on the desired operation. In this embodiment, an initial displacement input imparted to thumbwheel 112 is designated S1 and corresponds to an angular roation θ1. Consequently, a displacement S2 of flexible member 116 may be determined according to Equations (1) and (2), expressed in relation to the radius R1 to the outer circumference of thumbwheel 112 and the inner radius R2 about which flexible member 116 winds:

$$\theta 1 \times R1 = S1 \quad (1)$$

$$\theta 2 \times R2 = S2 \quad (2)$$

Rearranging Equation (2) in terms of θ1 yields Equation (3):

$$\theta 1 = S2/R2 \quad (3)$$

Substituting Equation (3) into Equation (1) gives Equation (4), which can then be rewritten in terms of S2 as Equation (5):

$$(S2/R2) \times R1 = S1 \quad (4)$$

$$S2 = (S1 \times R2)/R1 \quad (5)$$

Since the flexbile member 116 is coupled from thumbwheel 116 to spiral track 116 directly, the displacement S2 of thumbwheel 112 equals the displacement S3 of spiral track 116. Likewise, the input displacmement S3 of spiral track 116 may then be used to determine a deployment displacement output SD that will be imparted to outer sheath 108 (not shown in this view) based on the relationships between the angular rotation θ2, the initial radius R3 and final radius R5 of spiral track 116, as well as the radius R4 of the outer circumference of rotary reel 104. In particular, the input displacement S3 is equal to the product of initial radius R3 and angular rotation θ2 according to Equation (6) and may be rewritten in terms of the rotation as shown in Equation (7):

$$\theta 2 \times R3 = S3 \quad (6)$$

$$\theta 2 = S3/R3 \quad (7)$$

The same derivation applies to final radius R5, where the input displacement S3 is equal to the product of final radius R5 and angular rotation θ2 according to Equation (8) and may be rewritten in terms of the rotation as shown in Equation (9).

$$\theta 2 \times R5 = S5 \quad (8)$$

$$\theta 2 = S5/R5 \quad (9)$$

Therefore, the output displacement SD is equal to the product of angular rotation θ2 and the radius of rotary reel 104 R4 as shown in Equation (10), and Equation (7) or Equation (9) can be substituted to obtain Equation (11) giving the initial output displacement SDI when S3 is imparted at radius R3 or Equation (12) giving the final output displacement SDF when S3 is imparted at radius R5:

$$\theta 2 \times R4 = SD \quad (10)$$

$$SDI = (S3/R3) \times R4 \quad (11)$$

$$SDF = (S3/R5) \times R4 \quad (12)$$

Finally, Equations (11) and (12) may also be rewritten in terms of the thumbwheel 112 parameters of Equation (5) given that S2 equals S3, as indicated by Equations (13) and (14), respectively.

$$SDI = (S1 \times R2 \times R4)/(R1 \times R3) \quad (13)$$

$$SDF = (S1 \times R2 \times R4)/(R1 \times R5) \quad (14)$$

It will be appreciated that the final output displacement SDF is necessarily more rapid than the initial output displacement SDI due to the greater initial radius R3 as compared to the final radius R5 of spiral track 116. Accordingly, any of these configurations may be adjusted to obtain the desired amounts of initial and final output displacements.

Figure 6:
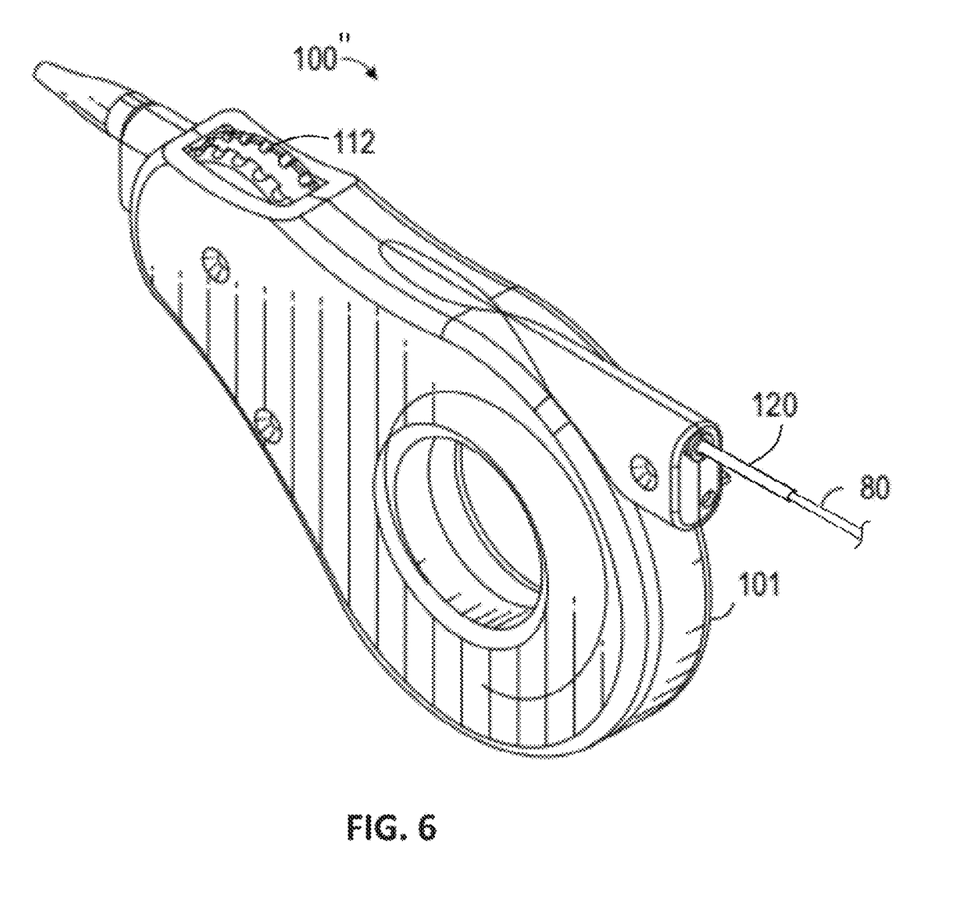
FIG. 6 illustrates yet another embodiment of FIG. 1A with an intermediate length of the housing and with the thumbwheel mounted close to the outer sheath and a tubular rapid deployment actuator.

Another rapid deployment embodiment is schematically depicted in FIG. 6. A tubular actuator 120 is secured at its distal end to rotary reel 104 and coaxially disposed over a proximal portion of inner shaft 80. Accordingly, a proximal portion of actuator 120 may be manipulated and withdrawn in a proximal direction to directly cause rotation of rotary reel 104 without the need to operate thumbwheel 112. Inner shaft 80 remains in its relative position as tubular actuator 120 is withdrawn. As desired, tubular actuator 120 may have a length such that it does not protrude beyond housing 101 until after outer sheath 108 has been withdrawn a given amount. Thus, thumbwheel 112 may be operated to initially expose stent 200 under fine control at its desired location within the patient, so that subsequent operation of actuator 120 completely deploys stent 200 in a more rapid manner.

Various materials may be selected for the components of the present invention, including any material having the desirable performance characteristics. In the particular embodiment shown in the drawings, the inner and outer shaft members and, strain relief and distal tip may be made of any biocompatible and suitably flexible yet sufficiently strong material, including polymers of various types. Possible selections for such materials include nylons or polyamides, polyimides, polyethylenes, polyurethanes, polyethers, polyesters, etc. In the alternative, some portion or all of the inner and/or outer shaft member may be formed of a flexible metal, including for example stainless steel or nitinol hypotube. The stent 200 is preferably made of any biocompatible material that is strong and rigid, including for example stainless steel, platinum, tungsten, etc. The components of the handle of the present invention are preferably made of a material that is strong and rigid, including for example inflexible polycarbonates, or even some metal components. In addition, the inner shaft member distal tip may preferably be provided with a through lumen adapted to receive a guidewire.

Of course, many different variations are included within the scope of the present invention. Some of these variations or alternative embodiments include any possible arrangement of sizes, materials, and designs within the scope of the claims.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A stent delivery system comprising
a catheter tip coupled to an inner shaft and an outer sheath with a stent disposed between the inner shaft and the outer sheath, the inner shaft and the outer sheath extending from a distal end to a proximal end;
a housing coupled to the inner shaft and outer sheath;
a rotary reel disposed in the housing and configured for rotation with respect to the housing, the rotary reel having a connector fixed to the outer sheath; and
a hypotube disposed in the housing and fixed thereto with the inner shaft extending into an opening of the hypotube and the outer sheath enshrouding a portion of the hypotube, the hypotube extending from a first end of the housing to a second end of the housing in a generally circular path defined by the rotary reel such that rotation of the rotary reel in a first direction pulls the outer sheath over the hypotube along the generally circular path to retract the outer sheath from the stent.

2. The stent delivery system of claim 1, further comprising a thumbwheel mounted to the housing and connected to the rotary reel.

3. The stent delivery system of claim 2, further comprising a ratchet disposed between the thumbwheel and the housing so that the thumbwheel is rotatable only in the first direction.

4. The stent delivery system of claim 2, further comprising a flexible member connecting the thumbwheel to the rotary reel.

5. The stent delivery system of claim 4, in which the flexible member is selected from a group comprising of a belt, rope, wire or combinations thereof.

6. The stent delivery system of claim 4, wherein the flexible member is secured to a spiral track of the rotary reel so that a rate of retraction of the outer sheath increases when withdrawn in a proximal direction.

7. The stent delivery system of claim 1, in which the rotary reel is disposed near the proximal end of the housing and the thumbwheel is disposed adjacent the outer sheath.

8. A catheter system comprising
a catheter tip coupled to an inner shaft and an outer sheath that partially surrounds the inner shaft and wherein both the inner shaft and the outer sheath extends from a distal end to a proximal end;
a housing coupled to the inner shaft and outer sheath;
a rotary reel disposed in the housing and configured for rotation with respect to the housing, the rotary reel having a connector fixed to the outer sheath; and
a hypotube disposed in the housing and fixed thereto with the inner shaft extending into an opening of the hypotube and the outer sheath enshrouding a portion of the hypotube, the hypotube extending from a first end of the housing to a second end of the housing in a generally circular path defined by the rotary reel such that rotation of the rotary reel in a first direction pulls the outer sheath over the hypotube along the generally circular path to retract the outer sheath with respect to the inner shaft.

9. A method for stent delivery, comprising:
providing a catheter tip coupled to an inner shaft and an outer sheath with a stent disposed between the inner shaft and the outer sheath, the inner shaft and the outer sheath extending from a distal end to a proximal end, a housing coupled to the inner shaft and outer sheath, a rotary reel disposed in the housing and configured for rotation with respect to the housing, the rotary reel having a connector fixed to the outer sheath and a hypotube disposed in the housing and fixed thereto with the inner shaft extending into an opening of the hypotube and the outer sheath enshrouding a portion of the hypotube, the hypotube extending from a first end of the housing to a second end of the housing in a generally circular path defined by the rotary reel;
positioning the stent at a desired location within a patient, and
rotating the rotary reel in a first direction to pull the outer sheath over the hypotube along the generally circular path to retract the outer sheath from the stent.

* * * * *